(12) United States Patent
Fischvogt et al.

(10) Patent No.: US 8,206,291 B2
(45) Date of Patent: Jun. 26, 2012

(54) PORTAL DEVICE

(75) Inventors: Gregory Fischvogt, Hamden, CT (US); Michael Bettuchi, Middletown, CT (US); Peter Hathaway, Lebanon, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 198 days.

(21) Appl. No.: 12/712,229

(22) Filed: Feb. 25, 2010

(65) Prior Publication Data
US 2010/0249517 A1 Sep. 30, 2010

Related U.S. Application Data

(60) Provisional application No. 61/163,909, filed on Mar. 27, 2009.

(51) Int. Cl.
*A61B 1/32* (2006.01)
(52) U.S. Cl. ...................................... 600/204
(58) Field of Classification Search .................. 600/235, 600/231, 210, 207, 208, 206, 115, 114, 204, 600/201; 604/174, 264, 275, 164.01, 164.03, 604/164.08, 164.09, 164.11; 606/185, 186, 606/108, 167, 220, 191, 194
See application file for complete search history.

(56) References Cited

U.S. PATENT DOCUMENTS

| | | | |
|---|---|---|---|
| 3,729,008 A | 4/1973 | Berkovits | |
| 3,890,977 A | 6/1975 | Wilson | |
| 4,321,002 A | 3/1982 | Froehlich | |
| 4,545,374 A * | 10/1985 | Jacobson | 600/210 |
| 4,719,917 A | 1/1988 | Barrows et al. | |
| 4,738,666 A | 4/1988 | Fuqua | |
| 5,071,429 A | 12/1991 | Pinchuk et al. | |
| 5,258,000 A | 11/1993 | Gianturco | |
| 5,279,564 A * | 1/1994 | Taylor | 604/104 |
| 5,391,156 A * | 2/1995 | Hildwein et al. | 604/174 |
| 5,415,635 A | 5/1995 | Bagaoisan et al. | |
| 5,423,858 A | 6/1995 | Bolanos et al. | |
| 5,468,248 A | 11/1995 | Chin et al. | |
| 5,968,069 A | 10/1999 | Dusbabek et al. | |

(Continued)

FOREIGN PATENT DOCUMENTS

EP 1747759 1/2007

(Continued)

OTHER PUBLICATIONS

Lendlein, et al., "Shape-memory polymers as stimuli-sensitive implant materials", *Clinical Hemorheology and Microcirculation* 2005, 32:105-116.

(Continued)

*Primary Examiner* — Pedro Philogene

(57) ABSTRACT

A surgical portal device includes a body portion defining a longitudinal axis and having a proximal end, a distal end, and a lumen configured to allow a surgical instrument to pass therethrough. At least one securing member is disposed in mechanical cooperation with the body portion and is longitudinally translatable with respect to the body portion between a first, non-actuated position and a second, actuated position. The one securing mechanism has a fixation segment configured to grasp tissue when the one securing member is in the second, actuated position to facilitate fixation of the body portion within the tissue. The body portion may include a channel. The one securing member may be disposed at least partially within the channel and is longitudinally translatable with respect to the channel.

13 Claims, 3 Drawing Sheets

U.S. PATENT DOCUMENTS

| | | | |
|---|---|---|---|
| 6,159,139 | A | 12/2000 | Chiu |
| 6,171,299 | B1 | 1/2001 | Bonutti |
| 6,235,869 | B1 | 5/2001 | Roby et al. |
| 6,358,266 | B1 | 3/2002 | Bonutti |
| 6,388,043 | B1 | 5/2002 | Langer et al. |
| 6,524,283 | B1 | 2/2003 | Hopper et al. |
| 6,551,282 | B1 | 4/2003 | Exline et al. |
| 6,589,208 | B2 | 7/2003 | Ewers et al. |
| 6,626,916 | B1 | 9/2003 | Yeung |
| 7,341,571 | B1 | 3/2008 | Harris et al. |
| 7,850,600 | B1 * | 12/2010 | Piskun ............ 600/114 |
| 2002/0095169 | A1 | 7/2002 | Maitland et al. |
| 2003/0236445 | A1 | 12/2003 | Couvillon |
| 2003/0236531 | A1 | 12/2003 | Couvillon |
| 2003/0236533 | A1 | 12/2003 | Wilson et al. |
| 2003/0236534 | A1 | 12/2003 | Kayan |
| 2004/0138702 | A1 | 7/2004 | Peartree et al. |
| 2004/0204723 | A1 | 10/2004 | Kayan |
| 2005/0082826 | A1 | 4/2005 | Werth |
| 2005/0149062 | A1 | 7/2005 | Carroll |
| 2005/0171562 | A1 | 8/2005 | Criscuolo et al. |
| 2005/0273138 | A1 | 12/2005 | To et al. |
| 2007/0038238 | A1 | 2/2007 | Freeman et al. |
| 2007/0106319 | A1 | 5/2007 | Au et al. |
| 2007/0203517 | A1 | 8/2007 | Williams et al. |
| 2007/0208276 | A1 | 9/2007 | Kornkven Volk |
| 2007/0225651 | A1 | 9/2007 | Rosenberg et al. |
| 2008/0015598 | A1 | 1/2008 | Prommersberger |
| 2009/0105655 | A1 | 4/2009 | DeSantis et al. |
| 2009/0105659 | A1 | 4/2009 | Bettuchi et al. |
| 2009/0105691 | A1 | 4/2009 | Sung |
| 2011/0009705 | A1 * | 1/2011 | Bombard et al. ............ 600/210 |

FOREIGN PATENT DOCUMENTS

| | | |
|---|---|---|
| EP | 1747772 | 1/2007 |
| EP | 1878391 | 1/2008 |
| EP | 2050404 | 4/2009 |
| EP | 2050405 | 4/2009 |
| EP | 2050406 | 4/2009 |
| WO | WO 02/00286 | 1/2002 |
| WO | WO 2004/052594 | 6/2004 |
| WO | WO 2004/060463 | 7/2004 |
| WO | WO 2004/105621 | 12/2004 |
| WO | WO 2005/000001 | 1/2005 |
| WO | WO 2007/038715 | 4/2007 |

OTHER PUBLICATIONS

Lendlein, et al., "Biodegradable, Elastic Shape-Memory Polymers for Potential Biomedical Applications", *Science* 2002, 296:1673-1676.

Lendlein, "Solving a knotty problem—surgical sutures from shape memorypolymers", *Materials World* 2002, 10(7):29-30.

Small, et al., "Laser-activated shape memory polymer intravascular thrombectomy device", *Optics Express* 2005, 13(20):8204-8213.

Faré, et al., "In vitro interaction of human fibroblasts and platelets with a shape-memory polyurethane", *Fibroblast/Platelet Interaction With SMPu* Wiley Periodicals, Inc. (2005), pp. 1-11.

Tim Thompson, "Polyurethanes as Specialty Chemicals Principles and Applications", 2005 CRC Press, Chapter 2: Polyurethane Chemistry in Brief.

\* cited by examiner

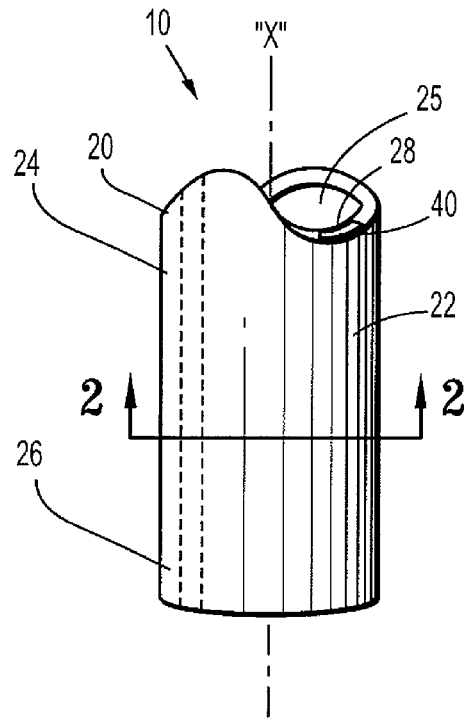
FIG. 1
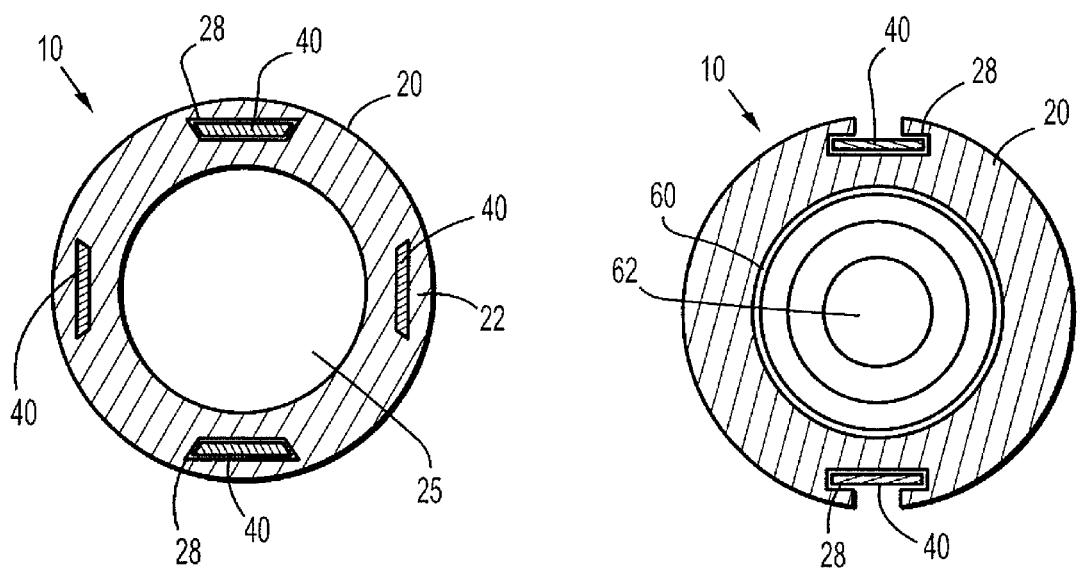
FIG. 2
FIG. 2A

PORTAL DEVICE

CROSS REFERENCE TO RELATED APPLICATION

The present application claims the benefit of and priority to U.S. Provisional Application Ser. No. 61/163,909 filed on Mar. 27, 2009, the entire contents of which are incorporated herein by reference.

TECHNICAL FIELD

The present disclosure relates to surgical ports. More particularly, the present disclosure relates to surgical port having port fixation components to secure the device relative to tissue of a patient.

DESCRIPTION OF THE RELATED ART

Surgical ports, such as introducers, trocars, and cannulas, permit the introduction of a variety of surgical instruments into a body cavity or opening within a patient. In procedures, such as endoscopic, laparoscopic or arthroscopic surgeries, a passage is created through tissue to access an underlying surgical site in the body. A port or cannula is positioned within the passage. Surgical instruments are introduced within the cannula to perform a surgical procedure.

It may be advantageous to provide a portal device that can be removably placed within an incision or body opening of a patient to selectively fix the access device therein.

SUMMARY

A surgical portal device includes a body portion defining a longitudinal axis and having a proximal end, a distal end, and a lumen configured to allow a surgical instrument to pass therethrough. At least one securing member is disposed in mechanical cooperation with the body portion and is longitudinally translatable with respect to the body portion between a first, non-actuated position and a second, actuated position. The one securing mechanism has a fixation segment configured to grasp tissue when the one securing member is in the second, actuated position to facilitate fixation of the body portion within the tissue. The body portion may include a channel. The one securing member may be disposed at least partially within the channel and is longitudinally translatable with respect to the channel. The one securing member is dimensioned whereby the fixation segment extends distally beyond the distal end of the body portion when the one securing member is in the second, actuated position. The fixation segment of the one securing member may be adapted to extend radially outwardly relative to the longitudinal axis when the one securing member is in the second, actuated position. The fixation segment of the one securing member may comprise a shape memory alloy. First and second securing members may be provided. The first and second securing members may be at least partially accommodated within respective channels of the body portion. A conformable pad may be mounted to the fixation segment. The conformable pad may comprise an elastomeric material. The fixation segment may define a general needle shape.

A surgical method is also disclosed. The surgical method includes the steps of:
  providing a surgical port, including:
    a body defining a longitudinal axis;
    a lumen extending through the body; and
    at least one securing member disposed in mechanical cooperation with the body;
  positioning the port at least partially within tissue;
  moving the one securing member relative to the body from a non-actuated position to an actuated position such that a fixation segment of the securing member is exposed from the body portion and grasps tissue;
  introducing a surgical instrument through the lumen of the body;
  performing a surgical procedure with the surgical instrument;
  returning the one securing member to the non-actuated position; and
  removing the port from the tissue.

The surgical port may include at least two securing members and, wherein during the step of moving, the at least two securing members are moved from the non-actuated position to the actuated position such that the respective fixation segments grasp tissue.

BRIEF DESCRIPTION OF THE DRAWINGS

Embodiments of the present disclosure will be better appreciated by reference to the drawings wherein:

FIG. 1 is a perspective view of a portal device in accordance with the present disclosure;

FIG. 2 is a cross-sectional view of the portal device of FIG. 1 across 2-2;

FIG. 2A is a cross-sectional view of another embodiment of the portal device including a seal assembly therein according to an embodiment of the present disclosure;

DETAILED DESCRIPTION OF THE EMBODIMENTS

Figure 3:
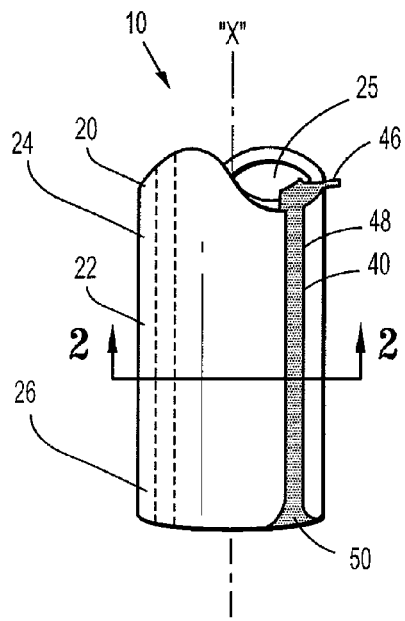
FIG. 3 is a perspective view of another embodiment of a portal device of the present disclosure in a retracted position.
Figure 4A:
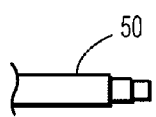
FIGS. 4A-4B are side and top views, respectively, of an embodiment of a fastener of the present disclosure having a bull nose configuration.
Figure 5A:
FIGS. 5A-5B are side and top views, respectively, of an embodiment of a fastener of the present disclosure having a needle-like configuration.

The device according to the present disclosure is suitable for facilitating the introduction of a surgical instrument into a surgical incision for performing endoscopic or laparoscopic procedures. It is envisioned that the device may be used in connection with other surgical procedures utilizing natural or formed openings in a body cavity of a patient. Embodiments of the present disclosure are illustrated in FIGS. 1-6B.

In the drawings and description which follows, the term "proximal," as is traditional, refers to the end of the surgical device or instrument of the present disclosure which is closest to the operator, while the term "distal" refers to the end of the device or instrument which is farthest from the operator.

Referring now to the drawings, in which like reference numerals identify identical or substantially similar parts throughout the several views. FIGS. 1 and 2 illustrate, in perspective and cross-sectional views, respectively, surgical portal device 10 in accordance with the principles of the present disclosure. Portal device 10 includes a body portion or portal body 20 and securing structure 40. Device 10 may be any device suitable for the intended purpose of accessing a body cavity, such as a trocar or cannula, and typically defines a passageway permitting introduction of surgical instrumentation therethrough. Portal device 10, therefore, may be integrally formed with a trocar or cannula assembly. In the alternative, a trocar or cannula assembly may be placed through or secured to portal device 10. Instrumentation includes a variety of surgical devices utilized through a portal, such as those used during laparoscopic or endoscopic surgery, as is within the purview of those skilled in the art.

Device 10 may be used in a variety of surgical applications and is particularly adapted for use in laparoscopic surgery where the peritoneal cavity is insufflated with a suitable gas, e.g., $CO_2$, to raise the cavity wall from the internal organs therein. Portal device 10 supports the walls of the opening in an open position so that surgical instruments may be passed therethrough. Device 10 may include a securing structure having fasteners or grips which may be deployed to anchor the device into the surrounding tissue so that the device cannot substantially shift or be inadvertently move and/or removed.

Device 10 is typically used with an obturator assembly (not shown) which may be blunt, a non-bladed, or a sharp pointed instrument positionable within the passageway of device 10. The obturator assembly is utilized to penetrate the abdominal wall and/or introduce device 10 at least partially through the abdominal wall. The obturator may then subsequently be removed from device 10 to permit introduction of surgical instrumentation utilized to perform the procedure through the passageway.

Portal body 20 may be a single monolithically formed unit or composed of several components connected to each other through conventional means, such as, for example, ultrasonic welding, or any other means envisioned by one skilled in the art. Portal body 20 may be formed of any suitable medical grade material, including metals such as stainless steel, titanium, and aluminum; other rigid materials, including polymeric materials such as polyetheretherketones, polycarbonate, polypropylene, polyethylene, and composites thereof. Portal body 20 may be manufactured for a single use or can be sterilized and reused.

Portal body 20 includes body portion 22 having proximal end 24 and distal end 26. Body portion 22 defines a longitudinal axis "x" extending along the length of body portion 22 and defines an internal longitudinal passageway or lumen 25 dimensioned to permit passage of surgical instrumentation (not shown). The cross-section of body portion 22, as shown in FIG. 2, is illustrated as a circular ring which forms the longitudinal passageway or lumen 25 whereby other surgical instruments may be placed such that body portion 20 aids in the insertion of instruments, implants, and other surgical related apparatus. Further, the shape of body portion 22 may provide stiffness to body portion 22 so that it will not bend under the counter force of tissue. At least one channel 28 is longitudinally disposed within body portion 22 and may extend from proximal end 24 to distal end 26. In the illustrated embodiment, channel 28 is substantially parallel to axis "x" of passageway 25.

In embodiments in which portal body 20 is used with laparoscopic procedures, portal device 10 may also be configured to seal the body opening to maintain the pneumoperitoneum while permitting the introduction of surgical instrumentation. It is envisioned that seal assembly 60, such as an instrument seal as illustrated in FIG. 2A, may be utilized. Seal assembly 60 defines one or more seal assembly openings 62 in general alignment with longitudinal axis "x". Seal assembly opening(s) 62 is configured and dimensioned such that insertion of a surgical instrument therethrough causes the material defining seal assembly opening 62 to engage the outer surface of the instrument in a substantially fluid-tight manner to minimize the formation of gaps around the surgical instrument and to help prevent fluids, such as gases, from escaping therethrough. An air-tight seal, such as a duck-bill seal, may be used in conjunction with or as an alternative to an instrument seal. The air-tight seal may include a slit which is adapted to close in the absence of a surgical object and/or in response to insufflation gases of the pressurized cavity.

It is envisioned that seal assembly may be fabricated from a relatively rigid material such as medical grade stainless steel or a biocompatible polymeric material, or formed from a resilient and/or flexible material such as a fabric, foam, elastomeric material, or combinations thereof in order to bend or deform about an inserted instrument while absorbing off-axis motion. A suitable seal assembly is disposed in commonly assigned U.S. Patent Publication No. 2005/0212221 to Smith et al., the entire contents of which are hereby incorporated herein by reference herein.

Channel 28 is a arranged coincident with axis "x" and, as illustrated in FIGS. 2 and 2A, channel 28 may be fully or partially enclosed by body portion 22 of portal body 20. Two and/or four channels are illustrated in the current embodiments, but it is envisioned that any number of channels may be disposed within body portion 22. Channel(s) 28 may be symmetrically or asymmetrically arranged about axis "x." Symmetry may provide increased stability to portal device 10 when in use. Channel 28 is configured and dimensioned to accommodate securing member 40. The shape of channel 28 is complementary to the shape of securing member 40.

Referring now to FIG. 3, securing member 40 is longitudinally slidable and/or extendable within channel 28 of portal body 20. In the illustrated embodiments, securing member 40 includes activation component 46 adjacent proximal end 24 of portal body 20, fixation segment 50 adjacent distal end 26 of portal body 20, and actuating member 48 extending along the length of channel 28 and connecting activation component 46 with fixation segment 50.

The size and dimension of securing member 40 may vary. In embodiments, securing member 40 may be uniform in size and diameter along the length of portal body 20. In other embodiments, securing member 40 may thicken, widen, and/or split towards distal end 26 of portal body 20. By increasing the periphery of securing member 40, more surface area is available for gripping tissue therewith. Accordingly, channel 28 of portal body 20 has a complementary geometry to accommodate securing member 40. Multiple securing members 40 may be used in conjunction with a single portal to allow tissue grip in multiple directions. In one embodiment, diametrically opposed securing members 40 are at least partially disposed within respective channels 28 of portal body 20.

Activation component 46 of securing member 40 is operably connected to actuating member 48 and accessible to the operator as it is located on proximal end 24 of portal body 20. Activation component 46 and actuating member 48 may be monolithically formed or connected by means within the purview of those skilled in the art as described above. Activation component 46 may be a button, plunger, tab, trigger, or other activation component within the purview of those skilled in the art to help distally and/or proximally translate actuating member 48 with respect to portal body 20. It is also envisioned that actuating member 48 may be translated without the assistance of activation component 46, for instance, remotely or by extending the length of actuating member 48 proximally beyond the length of channel 28. In an embodiment with multiple securing members 40, actuation component 46 may be operatively connected to each member 40 to simultaneously deploy the members 40. in the alternative, each securing member 40 may be individually deployed.

Figure 6A:
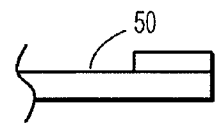
FIGS. 6A-6B are side and top views, respectively, of an embodiment of a fastener of the present disclosure having a pad and foot configuration.
Figure 4B:
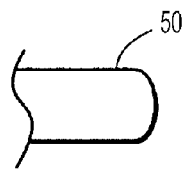
Figure 5B:
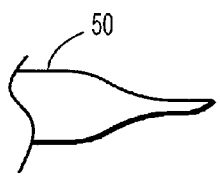
Figure 6B:
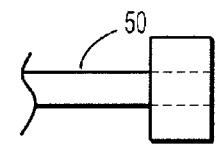
Figure 3A:
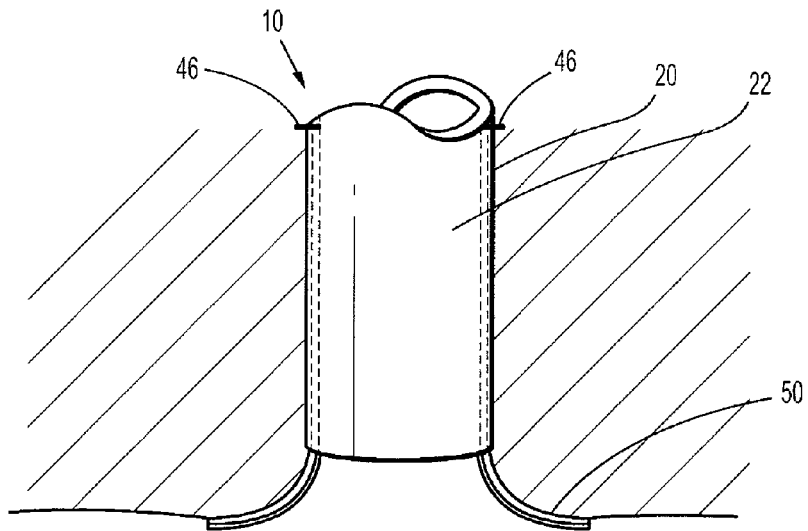
FIG. 3A is a perspective view of a portal device of the present disclosure in a deployed position.

Fixation segment 50 of securing member 40 is operably connected to or integral with actuating member 48 and maintained within channel 28 of portal body 20 in a pre-deployment, or retracted state. Fixation segment 50 and actuating member 48 may be monolithically formed or connected by means within the purview of those skilled in the art. Fixation segment 50 may be bull nose (FIGS. 4A-4B), needle shaped (FIGS. 5A-5B), or have a pad and foot configuration (FIGS. 6A-6B). Pad 52 may be mounted to fixation segment 50 and may comprise a compressible material such as an elastomeric material to conform to the tissue surfaces it engages to minimize trauma to the tissue. Fixation segment 50 may also be circular, oval, oblong, square, rectangular, or other regular or irregular shapes within the purview of those skilled in the art. Fixation segment 50 is dimensioned to emerge from distal end 26 of portal body 20 upon movement of actuating member 48 as illustrated in FIG. 3A.

Securing member 40 may be formed of spring steel. Spring steel has a very high resistance to creep under normal loads. Carbon or low-alloy steel may be processed to give it the hardness and yield strength needed in springs so that the steel may return to its original shape after bending, twisting, or other deformation. In embodiments, actuating member 48 is formed from spring steel so that upon actuation of activation component 46, actuating member 48 elongates to drive fixation segment 50 out of distal end 26 of portal body 20 and into surrounding tissue. In embodiments, fixation segment 50 may deflect in a radial outward direction relative to the longitudinal axis. Thus, with two opposed fixation segments 50, positive grasping with the tissue surrounding the passage is achieved. Fixation segments 50 may be dimensioned to embed within the tissue or engage an underlying tissue lining, e.g., the abdominal lining.

It is also envisioned that any portion or all portions of securing member 40 may be made of a material that expands with temperature or stress-induced conditions, such as shape memory alloys or polymers. Shape memory alloys (SMAs) are a family of alloys having anthropomorphic qualities of memory and trainability and are particularly well suited for use with medical instruments. One of the most common SMAs is Nitinol which can retain shape memories for two different physical configurations and changes shape as a function of temperature. Recently, other SMAs have been developed based on copper, zinc and aluminum and have similar shape memory retaining features.

SMAs undergo a crystalline phase transition upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austenite state to a martensite state with a change in temperature or stress-induced condition. This transformation is referred to as a thermoelastic martensite transformation.

Under normal conditions, the thermoelastic martensite transformation occurs over a temperature range which varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy. For example, Nitinol alloys can be fabricated so that the shape memory effect will occur over a wide range of temperatures, e.g., $-270°$ to $+100°$ Celsius.

Shape memory polymers (SMPs) may be used instead of, or may augment the use of, SMAs. SMPs are generally characterized as phase segregated linear block co-polymers having a hard segment and a soft segment. The hard segment is typically crystalline, with a defined melting point, and the soft segment is typically amorphous, with a defined glass transition temperature. In embodiments, however, the hard segment may be amorphous and have a glass transition temperature and the soft segment may be crystalline and have a melting point. The melting point or glass transition temperature of the soft segment is substantially less than the melting point or glass transition temperature of the hard segment.

When the SMP is heated above the melting point of the hard segment the material can be shaped. This shape can be memorized by cooling the SMP below the melting point of the hard segment. When the shaped SMP is cooled below the glass transition temperature of the soft segment while the shape is deformed, a new temporary shape can be set. The original shape can be recovered by heating the material above the glass transition temperature of the soft segment but below the melting point of the hard segment. The recovery of the original shape, which is induced by an increase in temperature, is called the thermal shape memory effect.

In embodiments where actuating member 48 is formed of shape memory alloys or polymers, it is envisioned that actuation of activation component 46 causes actuating member 48 to elongate to drive fixation segment 50 out of distal end 26 of portal body 20 and into and/or around surrounding tissue. In embodiments, fixation segment 50 is formed of shape memory materials such that the fixation segment 50 curls or turns out as illustrated in FIG. 3A, or otherwise deviates from longitudinal axis "x" upon deployment in order to grip or pierce tissue.

Figure 7:
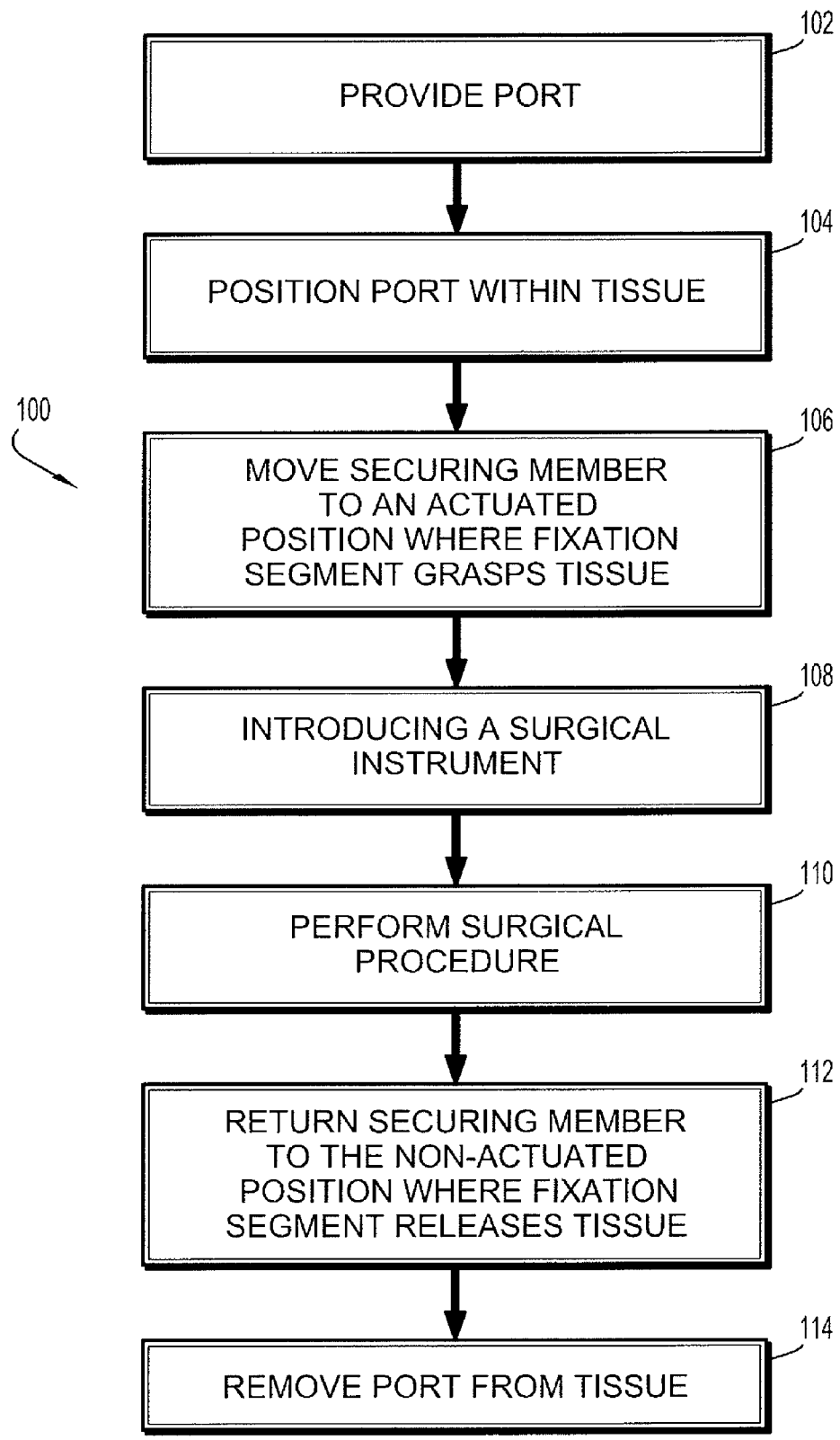
FIG. 7 is a flow chart illustrating a surgical method incorporating the portal device.

FIG. 7 is a flow chart illustrating a method of use of the portal device 10. In accordance with the method 100, the portal device 10 is presented to the surgical environment. (STEP 102). The portal device 10 is at least partially within tissue to provide access (STEP 104) to an underlying targeted body organ or tissue. The securing members which are initially disposed within the channels of the port, i.e., in a retracted or non actuated position, are moved relative to the body from the non-actuated position to an actuated position such that a fixation segment of the securing member is exposed from the body portion and grasps tissue. (STEP 106). This may be achieved, by depressing activation component 46 or otherwise causing actuating member 48 to longitudinally slide towards distal end 26 of portal body 20. Movement of actuating member 48 in turn, causes fixation segment 50 to emerge from distal end 26 of portal body 20 to grip, pierce or otherwise grasp surrounding tissue. Portal device 10, in a deployed position, is securely attached to the surgical port within the opening of the patient. A surgical instrument is introduced through the lumen of the body (STEP 108) followed by performance of a surgical procedure with the surgical instrument. (STEP 110) Upon completion, the operator may press or lift activation component 48 to return the port access device 10 back to the retracted position or non-actuated position. (STEP 112). The portal device may be removed from the tissue. (STEP 114)

It will be understood that various modifications may be made to the embodiments disclosed herein. Therefore, the above description should not be construed as limiting, but merely as an exemplification of preferred embodiments.

Those skilled in the art will envision other modifications within the scope and spirit of the present disclosure. Such modifications and variations are intended to come within the scope of the following claims.

What is claimed is:

1. A surgical portal device, comprising:
   a body portion defining a longitudinal axis and having a proximal end, a distal end, and a lumen configured to allow a surgical instrument to pass therethrough; and
   at least one securing member disposed in mechanical cooperation with the body portion and being longitudinally translatable with respect to the body portion between a first, non-actuated position and a second, actuated position, the one securing member having a fixation segment configured to grasp tissue when the one securing member is in the second, actuated position to facilitate fixation of the body portion within the tissue, and a conformable pad mounted to the fixation segment.

2. The device of claim 1 wherein the conformable pad comprises an elastomeric material.

3. The device of claim 1 wherein the fixation segment defines a general needle shape.

4. A surgical portal device, comprising:
   a body portion defining a longitudinal axis and having a proximal end, a distal end, at least one channel, and a lumen configured to allow a surgical instrument to pass therethrough; and
   at least one securing member disposed at least partially within the channel and being longitudinally translatable to slide within the channel between a first, non-actuated position and a second, actuated position, the at least one securing member having a fixation segment configured to grasp tissue when the one securing member is in the second, actuated position to facilitate fixation of the body portion within the tissue, wherein the fixation segment extends distally beyond the distal end of the body portion and is adapted to extend radially outward relative to the longitudinal axis when the one securing member is in the second, actuated position.

5. The device of claim 4, wherein the fixation segment of the one securing member comprises a shape memory alloy.

6. The device of claim 4, including first and second securing members, the first and second securing members being at least partially accommodated within respective channels of the body portion.

7. The device of claim 4, including at least three securing members, the at least three second securing members being at least partially accommodated within respective channels of the body portion.

8. The device of claim 4, including at least four securing members, the at least four securing members being at least partially accommodated within respective channels of the body portion.

9. A surgical method, comprising the steps of:
   providing a surgical port, including:
      a body defining a longitudinal axis and having proximal and distal ends;
      a lumen extending through the body; and
      at least one securing member disposed in mechanical cooperation with the body;
   positioning the body at least partially within tissue;
   moving the one securing member along the longitudinal axis such that the one securing member is distally advanced relative to the body from a non-actuated position to an actuated position such that a fixation segment of the securing member is exposed from the body and grasps tissue;
   introducing a surgical instrument through the lumen of the body;
   performing a surgical procedure with the surgical instrument;
   returning the one securing member to the non-actuated position; and
   removing the port from the tissue.

10. The surgical method of claim 9 wherein the surgical port includes at least two securing members and, wherein during the step of moving, the at least two securing members are moved from the non-actuated position to the actuated position such that the respective fixation segments grasp tissue.

11. The surgical method of claim 9, wherein the step of moving includes advancing the one securing member from the non-actuated position where the one securing member is confined by the body to the actuated position where the one securing member is exposed from the body.

12. The surgical method of claim 11, wherein the body defines a channel and wherein the step of moving includes sliding the one securing member within the channel.

13. The surgical method of claim 12, wherein the surgical port includes first and second securing members and wherein the step of moving includes sliding the first and second securing members within respective first and second channels defined by the body.

* * * * *